United States Patent
Agmont E Silva

(12) 
(10) Patent No.: US 10,653,807 B2
(45) Date of Patent: May 19, 2020

(54) SYSTEM, METHOD AND PROCESS FOR DISINFECTION OF INTERNAL SURFACES IN ASEPTIC TANKS AND PIPELINES BY FLOODING WITH SANITIZING FOG

(71) Applicant: AURRA SERVIÇOS ESPECIALIZADOS LTDA, São Paulo (BR)

(72) Inventor: Caio Vinicius Agmont E Silva, São Paulo (BR)

(73) Assignee: AURRA SERVIÇOS ESPECIALIZADOS LTDA (BR)

( * ) Notice: Subject to any disclaimer, the term of this patent is extended or adjusted under 35 U.S.C. 154(b) by 0 days.

(21) Appl. No.: 16/429,369

(22) Filed: Jun. 3, 2019

(65) Prior Publication Data

US 2019/0290793 A1    Sep. 26, 2019

Related U.S. Application Data

(63) Continuation of application No. 15/118,385, filed as application No. PCT/BR2014/000265 on Aug. 5, 2014, now abandoned.

(30) Foreign Application Priority Data

Feb. 20, 2014  (BR) .......................... 1020140039570

(51) Int. Cl.
*A61L 2/00* (2006.01)
*B05B 17/04* (2006.01)
(Continued)

(52) U.S. Cl.
CPC .................. *A61L 2/22* (2013.01); *A61L 2/24* (2013.01); *B08B 9/0327* (2013.01);
(Continued)

(58) Field of Classification Search
CPC ............ A61L 2/14; B08B 3/00; B08B 9/0325
(Continued)

(56) References Cited

U.S. PATENT DOCUMENTS 2,933,093 A    4/1960 Handyside
3,236,248 A    2/1966 Ray
(Continued)

FOREIGN PATENT DOCUMENTS

JP    2002066490 A1    3/2002

OTHER PUBLICATIONS

International Search Report dated Aug. 27, 2015 for International Application Serial No. PCT/BR2014/000265, International Filing Date—Aug. 5, 2014 consisting of 4-pages.

*Primary Examiner* — Monzer R Chorbaji
(74) *Attorney, Agent, or Firm* — Christopher & Weisberg, P.A.

(57) ABSTRACT

System, method and process for disinfection of internal surfaces in aseptic tanks and pipelines by flooding with sanitizing fog in facilities designed to store liquids in general, such system comprising an external equipment with means to generate sanitizing fog, controlling means of gases flow rate, in-line detectors and draining means of gases inside the tank, input means of fog carrying means comprising inert gases. Disinfection process comprises introduction of a sanitizing fog with droplets with a maximum size of 10 μm, preferably with maximum size of 5 μm, simultaneously with removal of gases enclosed inside such tanks and pipelines, maintaining a positive pressure inside such tanks and pipelines, such method providing reduction of oxygen concentration inside the tanks in two steps, the first one comprising reduction to near 10% and the second a reduction to a value below 1%, filling the tank with a sanitizing fog during the second step.

17 Claims, 2 Drawing Sheets

(51) Int. Cl.
  *B08B 9/00* (2006.01)
  *B08B 9/093* (2006.01)
  *A61L 2/22* (2006.01)
  *B08B 9/032* (2006.01)
  *A61L 2/24* (2006.01)

(52) U.S. Cl.
  CPC ........ *A61L 2202/11* (2013.01); *A61L 2202/14* (2013.01); *A61L 2202/16* (2013.01); *A61L 2202/18* (2013.01)

(58) Field of Classification Search
  USPC .................. 422/28, 300, 306; 239/4, 102.1; 134/22.1, 22.18, 24, 26, 56 R, 169 R, 110
  See application file for complete search history.

(56) References Cited

U.S. PATENT DOCUMENTS

| | | | | |
|---|---|---|---|---|
| 4,922,937 A | * | 5/1990 | Bloch | B08B 9/0325 134/22.12 |
| 5,711,819 A | * | 1/1998 | Miyasaki | B08B 3/00 134/11 |
| 7,159,598 B2 | | 1/2007 | Gregory | |
| 8,062,590 B1 | * | 11/2011 | Ricciardi | A61L 2/14 134/131 |
| 2004/0007255 A1 | * | 1/2004 | Labib | A61L 2/18 134/30 |

* cited by examiner

SYSTEM, METHOD AND PROCESS FOR DISINFECTION OF INTERNAL SURFACES IN ASEPTIC TANKS AND PIPELINES BY FLOODING WITH SANITIZING FOG

CROSS-REFERENCE TO RELATED APPLICATIONS

This application is a continuation of U.S. application Ser. No. 15/118,385, filed Aug. 11, 2016, which is a National Stage Application of PCT/BR2014/000265, filed Aug. 5, 2014, which claims priority to Brazilian Application Serial No. BR1020140039570 filed on Feb. 20, 2014, the entireties of which are incorporated herein by reference.

TECHNICAL FIELD

This present invention refers to a system, a method and a process of flooding by a sanitizing solution fog and disinfection of closed spaces such as storage tanks and associated pipelines thereto and, more particularly, internal surfaces of tanks and pipelines used in processing of liquids in general. Such liquids include, but are not limited to, vegetable juices, milk and its derivatives, beverages in general, alcoholic or not, products for household use and treated water.

BACKGROUND OF THE INVENTION

There is an increasing concern of customers related to health foods and fruit's juice has been revealed an important component of a healthy diet. Sector of industrialized juices is demonstrating a strong potential for increase, allowing the entrance of several companies into this market.

Juices for human consumption can be classified into five categories: I) natural juices: made directly from processing the fruit itself, squeezing or crushing it; II) powdered juices; III) concentrated juices: dehydrated natural juice with the purpose to reduce its volume; IV) ready to drink juices (nectar): composition made of juice's extract, water and several additives, such as sweeteners, flavoring, coloring and preservatives, to intensify, preserve and improve products features; V) pulp juices: characterized by absence, in their production, of any chemical and industrial preservation means or processes, being produced by freezing the pulp.

Orange juice is the most consumed in international market, and can be of two types, namely, concentrated and NFC.

The abbreviation NFC refers to juices "not from concentrate", i.e., juices not made from concentrated, whole and natural ones, with no addition of preservatives or any other chemical product. The technology for NFC juices is very recent. The firsts NFC orange juices arose in U.S.A. in the 90's.

NFC was an answer to consumer's market for a natural product, because so far the market was supplied only with concentrated or reconstituted juices.

In processing of concentrated juice, water is removed and the juice is concentrated in a ratio of up to 1:6. In the bottling plants, juice is reconstituted (water is added), bottled and marketed. This process impaired the juice's quality, since it interfered negatively in taste, vitamins' concentration and scent.

The principle behind NFC is to produce a natural juice during crop (in Brazil 6 months per year), pasteurizing and storing in large stainless steel tanks in aseptic conditions to be marketed in bulk to several countries in the world throughout the year.

The definition of aseptic process in food industry is understood as providing a sterilized product within sterile container. In the case of NFC orange juice in bulk, "containers" are very large stainless steel tanks with storage capacity up to 6 million liters.

The development of technology for huge aseptic tanks and the whole aseptic transport chain, including specific trucks and ships, had a very important role for large scale production of NFC orange juice and its commercialization in several markets all over the world. With this technology, it was possible to store NFC orange juice for periods up to one year and to bottle the final product in the consumer market.

Aseptic tanks must be kept in environment with controlled temperature around 1° C.

Aseptic tanks and pipelines must be free of oxygen, to avoid oxidation of the juice. Thus, NFC aseptic tanks work with nitrogen, which is also used to regulate internal pressure thereof.

In case of orange juice, there are aseptic tanks in the extraction plants, in the export terminals (Santos—Brazil) and in the ports of destination (The Netherlands, Belgium, USA), as well as in ships and containers (tanks).

Production of NFC natural juices of several fruits already exists, besides orange juice.

The major challenge of NFC juices industry is to preserve the quality of their products.

To this purpose, productive and logistic chains are seen as a whole and microbiological control must be present in all steps and places.

Being a natural product, juice is a product very susceptible to contamination. It is necessary to insure that all pipelines and transfer and storage tanks have internal surfaces totally sterilized and free of pathogens that could spoil the juice.

As an example of NFC orange juice, the process can be summarized, from production until storage, in the following steps:

Extraction of juice
Removal of pulp
Aseptic pasteurization
Transference and storage in aseptic tanks
Destination of product to final manufacturer (bottling)

The maintenance of aseptic state in every surface involved is extremely important in NFC process, considering that a single failure in disinfection process throughout the chain may compromise the integrity of millions of liters of juice.

In fact, the contact of products with surfaces poorly sanitized may increase the incidence of microorganisms, spoiling its intrinsic quality. In case of food products, lack of sanitization can lead to health problems, from a simple discomfort up to more severe consequences, such as intoxication or death.

Therefore, a very strict cleaning and sanitization program is adopted in plants, terminals, transportation trucks and ships.

All juice is tracked and product's samples are collected weekly for analysis.

The assurance of process is at cleaning and disinfection procedure and imperviousness of transfer lines and storage tanks.

The pipelines must be cleaned and disinfected after each juice passage between storage tanks, trucks and ships.

Disinfection of NFC aseptic tanks is an expensive and time-consuming process. It is mandatory when tanks are opened, whether for maintenance, or due to any problem of juice contamination.

Once opened, aseptic tank must be submitted to a very stringent cleaning and disinfection process before receiving juice again.

The average term to proceed with a cleaning and disinfection in a 6 million liters tank of NFC orange juice, performed in accordance with known techniques, takes about 20 days.

In summary, the process to release for use an aseptic tank comprises 3 steps:
1—Depressurization of the tank
2—CIP (clean in place) Process
3—Flooding (flooding in tank)

In first step, the tank is opened and all nitrogen is removed from inside. This process is performed through release valves placed on top of the tanks.

In the second step, CIP (Clean in Place) process is performed including cleaning and disinfection steps.

In this process, as generally used in the industry, tanks, pipelines and equipment are sanitized without disassembling.

Sanitizing procedure of surfaces in contact with products comprises two different and complementary steps: cleaning and disinfection.

Cleaning is complete removal of solid residues present in surfaces, such as grease, residual products, dust and other foreign matter, generally performed with alkaline detergents.

Disinfection, or sanitization, is the reduction in the amount of microorganisms in surfaces down to a level that does not compromise product's safety and suitability. This step can be performed physically (by heating) or chemically. In first case heat can be transferred to the surface using steam or hot water. The use of steam presents limited application due to high costs, slowness in process and reduced lifetime of some equipment.

Chemical disinfection is preferably used by industries. The chosen sanitizer must be compatible with the treated surface, have a broad spectrum microbiological activity, act quickly on microorganisms, be stable and resistant to presence of organic material, have low corrosive and toxicity and low cost. Peracetic acid is one of sanitizers that best fulfill the currently market's requirements.

Disinfection procedure is made by means of a CIP system that includes a set of tanks (water, caustic soda, phosphoric/nitric acid and peracetic acid), a pumping system with high flow rate, and apparatus for internal dispersal within the tank, such as spray ball, rotating spray or scan jet. This system works to insure that the cleaning/disinfection solution reaches all points of the tank, including the top portion. A CIP system must work with pressures above 8 Bar to provide a good impact of chemical solutions with the tank/pipeline walls to remove any solid residual impregnated on the walls.

The basic CIP process into a NFC orange juice tank consists on:
1—Initial rinse
2—Apply solution with 2% of caustic soda
3—Rinse with water to remove residual caustic soda
4—Lighting Test: performed by quality control to verify existence or not of solid material in tank internal surface. It's the validation method of the first step of CIP process. If the lighting test indicates the presence of residual material, steps 2 and 3 must be repeated
5—Application of a phosphoric/nitric acid solution, which works as stripper, helping to eliminate mineral matter, which can be deposited on tanks and pipelines' internal walls. This application complements step 2, above, in which caustic soda works as degreasing agent
6—Application of paracetic acid solution: used to high-level disinfection of tanks and pipelines' internal walls. It is used in a concentration between 500-3000 ppm, in accordance with the quality procedure adopted.

The third step is the most time consuming and expensive in the process. It refers to "Flooding", i.e., flooding aseptic tank by a liquid. This must be made with an aseptic liquid to avoid risk of contamination of the tank's internal surfaces.

Flooding works to remove all oxygen present in tank, which is necessary in case of products subject to oxidation, such as vegetable juices. However, in case of products not affected by presence of oxygen in tank, the flooding step can be omitted, as detailed herein later.

The most used methods of solution to flood tanks of NFC orange juice are:
a) Solution with sterile water: pasteurized water is used as a mean to flood the tank. The time to perform this process (manufacturing sterile water) varies in accordance with capacity and idleness of the available pasteurizer. If we consider as an example a pasteurizer with production capacity of 50,000 l/h, 120 hours will be necessary to produce enough sterile water for a tank of 6 million liters.
b) Iodoform solution: a solution of water plus iodoform is used. Due to high cost and its suitability to reuse, such solution in general is stored in a tank for a period of up to 1 year. The transfer of solution between tanks is made by pumping and lasts near to 2-3 days for a tank of 6 million liters. After one year this solution must be disposed of.
c) Peracetic acid solution: an option of sanitizer where iodoform is prohibited, such as in the European Community. It is a very expensive solution and difficult to reuse due to instability of peracetic acid.

After the tank flooding process, this tank is emptied. In this process $N_2$ is used, which is injected to occupy empty space and maintain the tank's internal pressure within its ideal value. The flood process performed in accordance with the known art can take between 6-10 days.

After this step, the tank is able to be loaded with NFC orange juice.

As can be noted, the flood step is the most time consuming, laborious and expensive of all cleaning and disinfection process of tanks. As drawbacks of this step, the following aspects can me mentioned (for a tank of 6 million liters):
High consumption of water: 6,000,000 liters
High consumption of sanitizer solution: 11,000 liters
High consumption of energy (in case of pasteurized water): 1000 Kw/hour×120 hs=120,000 Kw.
High disposal cost: solution must be treated with neutralizer and anti-foaming.
Loss of one storage tank.

As will be noted, the present invention presents significant advantages in comparison to current state of the art, the liquid flooding, with drastic reduction of involved resources in process. By way of comparison, we have:
Time spent in new procedure: 10 hours×6-10 days
Consumption of water: none×6,000,000 liters
Consumption of sanitizer solution: 50 liters×11,000 liters
Consumption of energy: 2 Kw/h×12 hs=24 Kw×120,000 Kw
Residue generation: 0×6,000,000 liters
Release of 1 tank to store NFC orange juice, with product's estimated value of US$2,5 million.

Sanitizing activities of facilities and equipment as well as practices of personal care are as important as production activities. This is easily demonstrated by the very large number of written procedures and instructions about cleaning and disinfection in several manufacturing steps.

Sanitization procedures must also be understood as being of interest to public health and environment.

There is a permanent challenge to establish a sanitization procedure that aims an increase of effectiveness and reduction of costs. Parameters involved in process, such as temperatures, concentrations, time and volume of solution must be reduced as much as possible. Saving water is a goal to be reached, by reducing its cost and subsequent reduction of effluent generation.

The disinfection step of a sanitization process made by a chemical agent is performed with a sanitizing solution in liquid state that must get in contact with every surface that gets in contact with product, for a minimum time, in accordance with concentration of sanitizer in solution. Depending on the size of surface being treated, the volume of consumed sanitizing solution can be from dozens of $m^3$ and time spent can be of a few hours. It means that there is a large consumption of water, sanitizer product, energy (pumps to provide circulation of solution) and effluents generation, that must be treated before being disposed to the environment.

Besides the drawbacks above mentioned, some disinfection processes in tanks and reservoirs are performed manually, where workers have to come inside confined spaces to proceed with application of sanitizer product. It is considered a high-risk activity, due to confined ambient and exposal of these people to toxic gases arising from the evaporation of sanitizing products.

Patent document WO2009043559, entitled Device and method for cleaning closed spaces, refers to a physical method based in use of steam generator, such steam introduced into a closed space for a controlled period, enough to transfer heat to the surface. However, the use of steam presents limited application due to high costs, slowness in process and reduced lifetime of some equipment.

U.S. Pat. No. 7,524,454, entitled Sanitation Method for Disinfection of Enclosed Spaces, describes a movable equipment containing a reservoir of sanitizing liquid in which piezoelectric elements are provided that, when being energized by ultrasonic frequency signals, originate a fog of droplets of such liquid, such fog being carried to an output nozzle through a fan. As indicated by the title, the invention aims disinfection of spaces, especially inhabitable spaces, such as rooms in buildings, in order to avoid proliferation of harmful microorganisms, such as fungi, bacteria and other biological agents. The method described in that document is not applied to sterilization of aseptic tanks and pipelines of large volume designed to store liquid products or similar.

Publication US2007/0224080, entitled Ultrasonic Sanitation Device and Associated Methods, describes an improvement of the previous patent, and is based in the same principles. Such improvements are mainly related to the construction of the device, and the document also details more completely the composition of used liquid, reciting the sanitizing agents. As in the above-mentioned document, its function is limited to sanitization of inhabitable environments, including houses, hospitals, and vehicles such as buses, ambulances, ships, and railroad cars among others. Equipment and method described within that document, however, are not applicable to sanitization of aseptic tanks and pipelines for liquid materials or the like.

Objects of Invention

In view of the above, the present invention aims, as the first object, to eliminate the need to perform flooding procedure with sanitizing solution in liquid state in NFC juices aseptic tanks or any other liquid product, whether ingestible or not, that need storage in aseptic tanks.

Other object is to reduce time spent in the flooding step of NFC juice tanks and in disinfection processes in tanks and pipelines in general, whether aseptic or not.

Other object is to reduce to the minimum production of effluents in flooding procedure of NFC juice tanks and in disinfection processes of tanks and pipelines in general, whose discard means additional costs to procedure and environmental risk.

Other object is to reduce consumption of chemical products, such as sanitizing products, in flooding procedures of NFC juice tanks and in disinfection processes of tanks and pipelines in general.

Other object is to save water in flooding procedure of NFC juice tanks and in disinfection process of tanks and pipelines in general.

Other object is to perform disinfection processes in tanks and reservoirs in general avoiding the need of people entering confined spaces, reducing, thus, occupational risk of such activity.

Other object is to reduce consumption of energy in flooding procedure of NFC juice tanks and in disinfection processes of tanks and pipelines in general.

Finally, other object is to assure quality of disinfection process in tanks, reservoirs and pipelines, insuring 100% of contact of internal surfaces of three-dimensional spaces by sanitizer product solution, in flooding procedure of NFC juice tanks and in disinfection processes of tanks and pipelines in general.

SUMMARY OF INVENTION

The above objects, as well as others, are reached by means of flooding into a three-dimensional space—in the present instance, aseptic pipelines and tanks to store NFC juices—a fog of a sanitizing solution with droplets smaller than 10 microns and, preferably, smaller than 5 microns, instead of a liquid solution, such fog being generated by an equipment outside said aseptic storage tank, pipelines and associated aseptic connections, such fog being introduced into the aseptic tank and/or pipelines through channels commonly used to fill and empty its content.

In accordance with another feature of the invention, such equipment includes a nebulization tank, maneuvering valves to control entrance of said fog's carrier gas as well as to control removal of atmospheric air in NFC aseptic tank, control panel and a microbiological filter to filter the carrier gas.

In accordance with another feature of the invention, such sanitizing solution fog is produced by means of piezoelectric elements installed in the nebulization tank and driven by a high frequency generator.

In accordance with another feature of invention, such nebulization tank is filled with a sanitizing solution whose level is controlled by a level detector installed in the tank.

In accordance with another feature of invention, the sanitizing solution is fed into the nebulization tank by a peristaltic pump whose operation is controlled by such level detector.

In accordance with another feature of invention, the means that carry the sanitizing solution fog to the inside of aseptic tank and/or pipelines can be air or an inert gas.

In accordance with another feature of invention, such inert gas is nitrogen.

In accordance with another feature of the invention, such carrying means is filtered by a microbiological filter, before entering the nebulization tank.

In accordance with another feature of the invention, atmospheric air inside the NFC juice aseptic tank is removed by suction through controlled means provided in said equipment.

In accordance with another feature of the invention, said means comprise a centrifugal fan controlled by a frequency inverter circuit.

In accordance with another feature of the invention, said external equipment is provided with casters, consisting of a mobile equipment.

DESCRIPTION OF DRAWINGS

Other advantages and features of the invention will become more evident from the description of a preferred embodiment, given as a non-limiting example, and from accompanying drawings where.

DETAILED DESCRIPTION OF INVENTION

As already mentioned herein, the flooding procedure is the final step of cleaning and disinfection process of NFC juices aseptic tanks. The system of the present invention eliminate the need to perform said flooding with a liquid sanitizing solution, therefore saving time, chemical products, water, energy and reduction of effluents.

In the known flooding procedure, i.e., using a sanitizing solution in liquid state, an iodoform solution must be transferred to NFC juice aseptic tank with pumps. Said sanitizing solution enters the aseptic tank by means of a bottom valve 52 situated in base of aseptic tank 50 (see FIG. 2). As soon as the sanitizing solution begins to fill the tank, the atmospheric air within is expelled by a relief valve 46 situated on top of the aseptic tank. The cost of providing a iodoform solution for a 6 million liters aseptic tank is about US$ 120,000.00. The time to fill the whole aseptic tank and expel all atmospheric air is from 2 to 4 days and will depend on flow rate of the pump used to transfer the solution.

Figure 2:
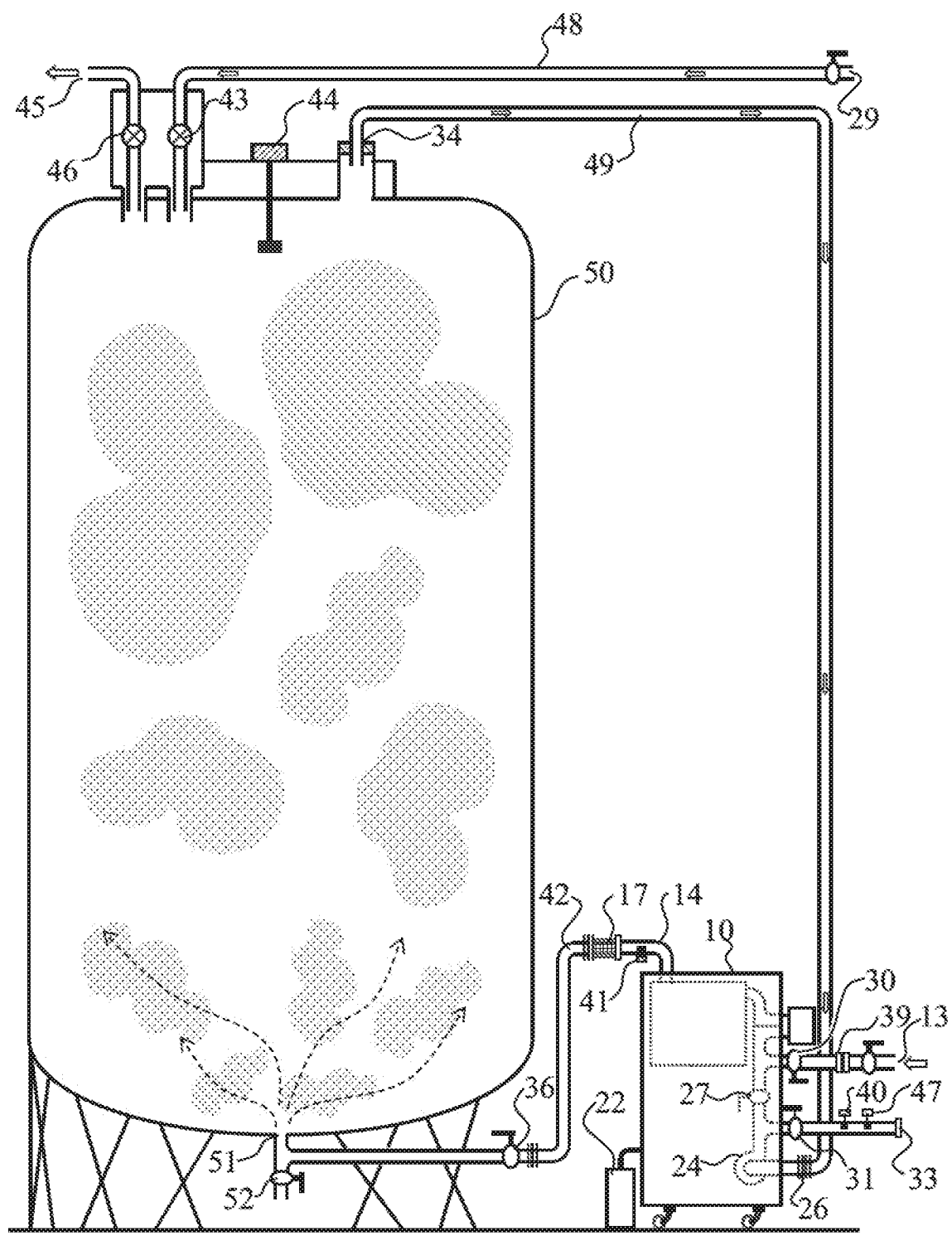
FIG. 2 illustrates the use of the invention when flooding an aseptic storage tank with sanitizing fog and gas.

Once the aseptic tank is completely filled with sanitizing solution and confirmation that there is no longer any atmospheric air inside, the procedure to empty the tank is initiated. To maintain internal pressure of tank, nitrogen is injected by valve 43 situated on top of tank, as shown in FIG. 2.

Due to its high cost, such solution must be transferred to another tank, in order to not waste it, as it can be reused in up to 1 year. Thus, 1 aseptic tank is lost to store NFC juice. The emptying procedure of aseptic tank also lasts from 2 to 4 days. Once the tank is emptied, there is a sterile tank and able to receive NFC juice.

The inventive concept now proposed consists of generating a fog of sanitizing solution with a carrying gas, to insure that substitution of gases inside the aseptic tank (atmospheric air by nitrogen) is performed in a sterilized manner, avoiding, thus, contamination of aseptic tank in this procedure step. In case of NFC juices, an inert gas is used as carrying means, being that, in alternative embodiments, such carrying means can be air itself.

The fog of sanitizing solution has the same features of sanitizing solution in liquid state. In fact, it is the same solution. The difference is that it works with a droplet size of, approximately, 5 microns, which increases the contact surface area of sanitizer solution. Thus, the same three-dimensional space can be occupied, reaching 100% of its internal surfaces, using only a small amount of the solution that would be necessary if a solution in liquid state were used.

Figure 1:
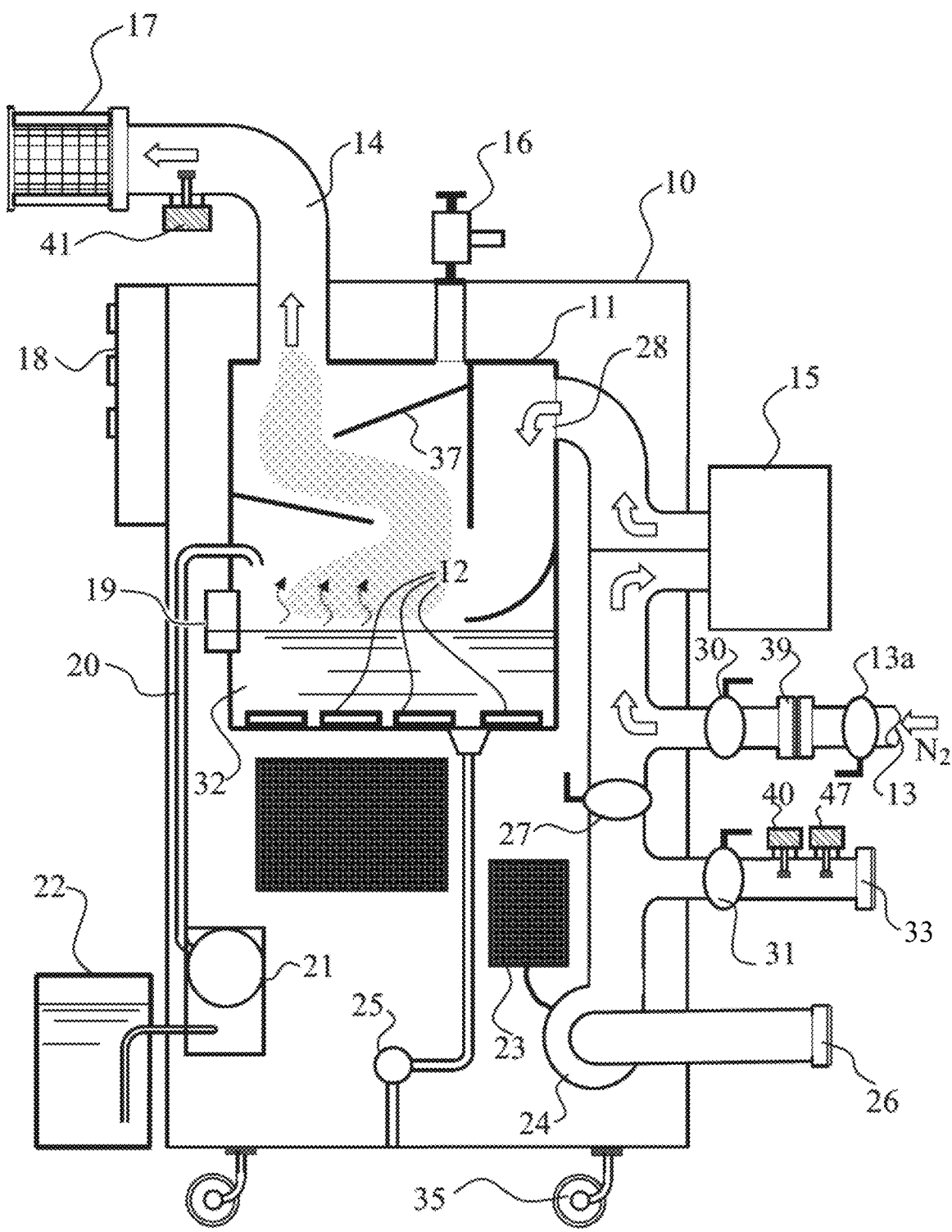
FIG. 1 shows the equipment that produces the fog of sanitizing solution, according to the invention.

Referring now to FIG. 1, the invention comprises an external equipment housed into a cabinet 10, which is provided with casters 35 that make it movable near several equipments (tanks and pipelines). Inside this cabinet there is the nebulization box 11, made of stainless steel 304/316 able to resist internal pressures up to 10 bar. Such nebulization box has a pressure relief valve 16 regulated to open with 6 Bar.

Such box 11 is where the liquid solution becomes a fog. The bottom of this box is provided with piezoelectric elements 12, whose number depends on desired volume of fog production. Such plates must be made of stainless steel or material resistant to corrosive solutions.

The level control of sanitizing solution 32 is essential to a proper operation of the system, since fog production can be impaired in case the column of solution above the plates' surfaces 12 exceeds 50 mm. Such control is made by a group of components that include detector 19, peristaltic pump 21, drainage system 25 of nebulization tank, reservoir of sanitizer solution 22 and a supplying conduit of solution 20. Information from detector 19 indicates if the level of sanitizer solution is below or above ideal value; in first case, peristaltic pump 21 is driven sending solution included in reservoir 22 to the box 11, through conduit 20. In the second case, drainage system 25 is driven in order to remove part of solution included in nebulization box.

The piezoelectric transducers are driven by electronic circuits that generate an ultrasonic signal in the order of hundreds of kHz to some MHz, wherein the size of fog drop produced is related to such frequency.

The nebulization box is provided, further, with deflectors 37 that work to condensate large drops generated in procedure.

The gaseous carrying means, in case nitrogen, is introduced in box 11 through input 28, wherein the function of such means is to draw the fog produced inside the nebulization box out of the equipment.

Depending on use of the system, atmospheric air itself can also be used as carrying means, instead of inert gases, or even compressed air.

In case of application in aseptic tanks it is necessary to insure the quality of carrying means. Thus, before going inside nebulization box, the carrying means, more specifically nitrogen, passes by a filter 15 comprising a stainless steel housing and a microbiological cartridge of known type.

In operations carrying means is provided by an external piping 13, a pressure relief valve 16 must be provided installed on top portion of nebulization box as a safety measure, since a very high pressure can cause excessive pressurization inside the box 11.

The fog produced is carried to the output pipeline 14, which is provided by an in-line detector 41 to monitor gas flow rate. Sanitizing fog is launched inside pipelines and tanks by hoses attached to equipment output; quantity and quality of produced fog can be monitored by glass monitor window 17 allowing visual inspection.

At one side of equipment control a panel 18 is installed, wherein elements for electrical protection are found (switches, relays, etc.), as well as controllers to perform equipment operation manually or automatically. Depending on the application, said control panel can be provided with CLPs, timers, delayers or other controllers, in accordance with application.

The equipment is provided with a centrifugal fan 24, used in several steps of the inventive method, whose operation, described later, is controlled by an electronic inverter module of variable frequency 23 headed by control panel 18.

Several maneuver valves 27, 30 and 31 are part of the equipment that are driven during different steps of sanitization process of tank, as will be described herein below.

The method used in invention, which is detailed below, refers to a process of gaseous flooding of an aseptic tank, designed to store NFC orange juice, with capacity up to 6.000.000 liters. FIG. 2 describes interconnections of such aseptic tank with the equipment that generates such sanitizing fog, shown in FIG. 1. The aseptic tank is placed inside a cold chamber with controlled temperature of 1° C., which is not shown in the drawings.

The gaseous flood process includes two stages, the first one consisting of substitution, even partially, of atmospheric air, which contains oxygen, by nitrogen, inside the tank. The second stage includes application of sanitizing fog.

The main steps of the first stage are as follow:
a. after the end of CIP process, wait at least 4 hours in order to complete the liquid runoff from internal walls of tank 50, which is collected in bottom and drained through opening 51 and correspondent valve 52, illustrated in FIG. 2;
b. place the equipment 10 near tank 50 and make the following attachments, with all valves closed:
connect a hose 42 between bottom valve 36 of tank and the viewer 17 of output 14 from such equipment;
connect nitrogen source 13 to flange 39, keeping all valves closed 27, 30 and 31 of equipment 10 as well as valve 13a from nitrogen piping;
interconnect by means of a hose 49 the inspection flange 34 on top of tank 50 and an air input 26 associated to centrifugal fan 24 in equipment 10, the output of such fan discharging at atmosphere through output 33, out of cold chamber;
connect to exterior of cold chamber the pressure relief valve output 16 by means of a hose;
put the sanitizing solution reservoir 22 next to equipment 10 and place the end of suction hose of peristaltic pump 21 inside this reservoir;
c. check the proper installation of in-line detectors 40 (oxygen), 41 (gases flow rate) and 47 (hydrogen peroxide);
d. install microbiological cartridge in filter 15;
e. connect control panel 18; peristaltic pump 21 is driven automatically, transferring a portion of sanitizing solution from reservoir 22 to nebulization box 11, until reaching the correct level indicated by level detector 19;
f. after opening the bottom valve 36, slowly open input valve of nitrogen 30, as well as valve 13a, monitoring pressure inside the tank with detector 44;
g. using frequency inverter command in control panel 18, drive centrifugal fan 24, setting the frequency (and, therefore, the fan flow rate) in order that volume exhausted through output 33 to exterior is approximately equal to volume of injected nitrogen. By performing this adjustment, data from detector 44 must be controlled, in order to assure a positive pressure value in tank, avoiding that such pressure becomes negative.

At this point, nitrogen is entering into equipment 10 through valve 30, passing by filter 15 and, after going through nebulization box 11, leaves by output duct 14 and viewer 17 to hose 42 which introduces the gas in tank 50 through valve 36. Inside the tank the nitrogen "pushes" oxygen to the upper portion of tank, from where is suctioned by centrifugal fan 24 through inspection flange 34 and duct 49 and released to atmosphere through discharge opening 33. During such period, oxygen detector 40 is monitored; initially, such detector should show a value near to 20.6%, corresponding to the oxygen concentration in atmospheric air. As time goes by, this concentration must fall, due to introduction of nitrogen in tank. Upon reaching a value of approximately 10%, the second stage of procedure is initiated, described as follows:
by setting frequency inverter, reduce in approximate 50% flow rate in centrifugal fan 24;
in control panel 18, turn on the nebulization system ("fog") to energize piezoelectric transducers 12 to produce sanitizing fog inside nebulization box 11;

The nitrogen flow introduced in input 28 will carry with it such fog, which must be checked in a visible manner by viewer 17. Such fog, forwarded by pipeline 42 and bottom valve 36, enters the tank, occupying gradually its whole interior.

The purpose of this stage consists of filling the complete volume of tank with sanitizing fog and nitrogen. During such operation, the sanitizing solution inside nebulization box 11 will be consumed. The level detector 19 sends an electrical signal to control panel in order to drive the peristaltic pump 21, which will transfer more sanitizing solution from reservoir 22 to interior of nebulization box 11 to maintain the proper level of solution.

After some hours, it will be possible observe part of sanitizing fog exiting to the atmosphere through exhaustion duct 33 of equipment 10. At this point, there will be possible to measure concentration of sanitizer through detector of hydrogen peroxide 47. During such step the concentration of oxygen continues to be monitored by detector 40 and also the internal pressure of tank through pressure detector 44, because there exists a trend to a gradual increase of internal pressure of the tank.

This stage lasts approximately 8 hours, considering that it is stopped when concentration of oxygen falls below 1% and the concentration of peracetic acid is within the limit determined by quality control department of the company.

Once the predetermined values of concentration of oxygen and peracetic acid are reached, the second stage of operation is ended:
ultrasonic plates 12 are deactivated;
the valve 30 of nitrogen input is closed;
inspection flange 34 on top of tank is substituted by a closing flange; valve 31 is closed;
the bottom valve 36 is closed and hose 42 is disconnected.

From this point, the tank is totally closed, but not necessarily in desired pressure. Leaving the valve 29 open, the pressure is automatically controlled by the system through opening and closing of valve 43, in order to introduce necessary amount of nitrogen to reach the ideal pressure. The tank, now, is in conditions to be supplied with NFC juice.

Although the flooding method has been described based on the oxygen removal from a fixed tank, designed to store orange juice, it is understood that principles of invention are applicable to disinfection of movable tanks, such as those used in road transportation using trucks, railways using wagons and maritime using ships.

Furthermore, as mentioned before, sanitizing fog can be used at CIP step, more specifically at step of disinfection/sanitization of tanks and pipelines, which is performed after cleaning respective surfaces using caustic soda and acid. In comparison to known methods, in which sanitizing solution is applied by means of pumps, spray ball, rotating spray or scan jet, use of sanitizing fog presents the advantage of reaching all internal surfaces of tank and associated pipelines, besides substantial economy of water and product used as disinfectant.

In general lines, the disinfection/sanitization process includes some of the steps related to the second step of gaseous flood process previously detailed. Notice that, however, as a significant difference, the fact that, in disinfection/sanitization, the carrying means is not necessarily nitrogen, but may be a gas or mixture of gases (such as atmospheric or compressed air).

Considering that carrying means is atmospheric air, such disinfection will comprise, therefore, the following steps:

i. after the end of cleaning process (caustic soda-rinse-acid-rinse), wait at least 4 hours in order to complete liquid runoff from tank's internal walls 50, which is collected in bottom and drained through opening 51 and correspondent valve 52, illustrated in FIG. 2;
ii. place the equipment 10 near to tank 50 and connect a hose 42 between bottom valve 36 of tank and viewer 17 of output 14 of such equipment;
iii. put the sanitizing solution reservoir 22 next to equipment 10 and place the end of suction hose of peristaltic pump 21 inside this reservoir;
iv. connect control panel 18; peristaltic pump 21 is driven automatically, transferring a portion of sanitizing solution from reservoir 22 to nebulization box 11, until reaching the correct level indicated by level detector 19;
v. in control panel 18, turn on the nebulization system ("fog") to energize piezoelectric transducers 12 to produce sanitizing fog inside nebulization box 11;
vi. connect centrifugal fan 24 and set the frequency inverter 23 to initiate drag of sanitizer fog.

Regarding the step of disinfection of CIP process there are 2 ways of proceeding:

1—Without looping: in this case atmospheric air must go into the equipment 10 through input 26, pass by centrifugal fan 24, pass by filter 15, enter the box 11 and leave by duct 14. In this case air inside of the tank will not be removed (through valve 34 and duct 49), but only an injection of sanitizing fog in tank or pipeline. The valves 30 and 31 remain closed, being opened the valve 27.

2—With looping: refers to looping the fog inside the tank or net of pipeline. In this case, output 34 of tank is connected to input 26 by the duct 49. Therewith, by centrifugal fan 24, fog solution loops inside the tank. The valve 27 remains opened and valves 30 and 31 closed.

Once concluded disinfection/sanitization of tank and associated pipelines, the sequence of process will depend on the nature of stored product, as well as carrying means of sanitizing fog. Thus, in case the air was used as carrying means and the product is a NFC vegetable juice, oxygen removal process will be necessary in accordance with flood procedure already mentioned before.

When stored product is not affected by oxygen, it is possible to proceed immediately to tank's filling, it being not necessary, in this case, to proceed with gaseous flood procedure.

Accordingly, the invention is defined and bounded by the set of the following claims.

The invention claimed is:

1. A method for disinfection of internal surfaces of at least one of an aseptic tank and a pipeline configured to store and transport liquids, the method comprising:
flooding the at least one of the aseptic tank and the pipeline with an inert gas and a sanitizing fog, the flooding causing oxygen present in the tank to rise to the upper portion of the tank;
detecting the concentration of oxygen in the tank;
removing the oxygen from the at least one of the aseptic tank and the pipeline through a duct and into the atmosphere; and
closing the duct when the detected concentration of oxygen in the tank is less than a predetermined amount.

2. The method of claim 1, wherein the sanitizing fog comprises droplets having a maximum size of 10 μm.

3. The method of claim 1, wherein the sanitizing fog comprises droplets having a maximum size of 5 μm.

4. The method of claim 1, wherein the sanitizing fog comprises a peracetic acid solution.

5. The method of claim 4, wherein the peracetic acid solution has a concertation ranging from 500 to 3000 ppm.

6. The method of claim 1, wherein the predetermined amount of the concentration of oxygen is less than 1%.

7. The method of claim 1, wherein the sanitizing fog is produced by oscillation of piezoelectric transducers driven by an ultrasonic oscillator circuit.

8. The method of claim 7, wherein the method further comprises:
reducing a content of oxygen inside the tank to less than 10% before the flooding.

9. A method for disinfection of internal surfaces of at least one of an aseptic tank and a pipeline configured to store and transport liquids, the method comprising:
generating a sanitizing fog;
flooding the at least one of an aseptic tank and a pipeline with an inert gas and the generated sanitizing fog, the flooding causing oxygen present in the tank to rise to the upper portion of the tank; and
measuring a concentration of oxygen in the at least one of the aseptic tank and the pipeline;
removing the oxygen from the at least one of the aseptic tank and the pipeline through a duct and into the atmosphere until a predetermined concentration of the oxygen is reached.

10. The method of claim 9, wherein the flooding is simultaneous with the removal of the oxygen, the oxygen being removed using a centrifugal fan whose output discharges to the atmosphere.

11. The method of claim 9, wherein the sanitizing fog comprises droplets having a maximum size of 10 μm.

12. The method of claim 9, wherein the sanitizing fog comprises droplets having a maximum size of 5 μm.

13. The method of claim 9, wherein the sanitizing fog comprises a peracetic acid solution.

14. The method of claim 9, wherein the peracetic acid solution has a concertation ranging from 500 to 3000 ppm.

15. The method of claim 9, wherein the inert gas is nitrogen.

16. The method of claim 9, wherein the sanitizing fog is produced by oscillation of piezoelectric transducers driven by an ultrasonic oscillator circuit.

17. The method of claim 9, wherein the predetermined concentration of oxygen is less than 1%.

* * * * *